United States Patent
Authelin et al.

(10) Patent No.: US 7,041,318 B2
(45) Date of Patent: May 9, 2006

(54) MILLING PROCESS FOR THE PRODUCTION OF FINELY MILLED MEDICINAL SUBSTANCES

(75) Inventors: Jean-Rene Authelin, Saint Germain les Arpajon (FR); Patrick Hosek, Kronberg im Taunus (DE)

(73) Assignee: Aventis Pharma Limited, West Malling (GB)

( * ) Notice: Subject to any disclaimer, the term of this patent is extended or adjusted under 35 U.S.C. 154(b) by 0 days.

(21) Appl. No.: 09/871,876

(22) Filed: Jun. 1, 2001

(65) Prior Publication Data

US 2002/0114766 A1    Aug. 22, 2002

Related U.S. Application Data

(63) Continuation of application No. PCT/GB99/04047, filed on Dec. 1, 1999.

(51) Int. Cl.
*A61K 9/00* (2006.01)
*A61K 9/14* (2006.01)
*A61K 31/357* (2006.01)

(52) U.S. Cl. .............. 424/489; 424/400; 514/463

(58) Field of Classification Search ............. 424/434, 424/400, 489; 514/463
See application file for complete search history.

(56) References Cited

U.S. PATENT DOCUMENTS

| | | | | |
|---|---|---|---|---|
| 3,897,010 A | * | 7/1975 | Weishaupt et al | 241/18 |
| 4,767,612 A | * | 8/1988 | Hagen et al. | 424/434 |
| 4,810,488 A | * | 3/1989 | Jinks | 424/45 |
| 5,562,923 A | | 10/1996 | Trofast et al. | |
| 5,637,620 A | | 6/1997 | Trofast et al. | |
| 5,747,002 A | | 5/1998 | Clark et al. | |
| 6,145,765 A | * | 11/2000 | Capelle et al. | 241/39 |

FOREIGN PATENT DOCUMENTS

| | | |
|---|---|---|
| EP | 0336787 | 10/1989 |
| EP | 0 407 028 B2 | 7/1999 |
| GB | 1481304 | 7/1977 |
| WO | WO 97/32688 | 9/1997 |
| WO | WO 98/31352 | 7/1998 |

OTHER PUBLICATIONS

The Merck Index, 11(1511) 1989.

* cited by examiner

*Primary Examiner*—Thurman K. Page
*Assistant Examiner*—Simon J. Oh
(74) *Attorney, Agent, or Firm*—Kelly Bender; Paul Darkes

(57) ABSTRACT

The present invention is a method of milling materials to form a fine powder with a median particle size below 10 micrometer which is suitable for inhalation and which has substantially no amorphous content generated during milling. The method is particularly suitable for milling materials which are soft. The method comprises milling the material in a fluid energy mill at reduced temperature using helium, or helium mixed with another gas, as milling fluid. Temperatures of −30° C. or less are used.

8 Claims, No Drawings

MILLING PROCESS FOR THE PRODUCTION OF FINELY MILLED MEDICINAL SUBSTANCES

This application is a continuation of International Application No. PCT/GB99/04047, filed Dec. 1, 1999, incorporated herein by reference.

The present invention relates to a process for the production of finely milled medicinal substances intended for use as inhalation medicaments.

Inhalation medicaments must have a fine particle size in order to penetrate deep into the lungs where they can be absorbed. Typically particles less than 10 microns in size are required. Such fine particles are normally prepared by milling the material to be inhaled. It is well known that the intensive milling required to produce these fine particle sizes can produce profound changes in the crystal structure of the material being milled. The exact changes are governed by the nature of the starting material but commonly freshly milled powders have a greatly increased content of amorphous phase. This initially forms on the surface of the particles but can constitute a large proportion of the total weight of the powder.

Changes in crystal structure, including increase in amorphous content, can cause a number of problems. The particles tend to stick together, making the freshly milled powder extremely cohesive. With time, often under the influence of ambient moisture, the surface phase tends to revert to its more stable original phase. This can cause the particles to be welded together. Furthermore, the crystal form of a pharmaceutical substance can have a significant effect on its potency, as discussed by J. I. Wells in Pharmaceutical Preformulation: The Physiochemical Properties of Drug Substances, John Wiley & Sons, New York (1988). We have now found that by careful control of the milling conditions used we can achieve the required particle size for an inhalation medicament without generating amorphous phases on the surface of the powder.

U.S. Pat. No. 5,562,923 describes a method for producing finely milled highly crystalline medicinal substances intended for use as inhalation medicaments by drying the milled medicament, treating with a non aqueous solvent and then drying. U.S. Pat. No. 5,637,620 uses a different method; the milled medicament is conditioned under controlled conditions of temperature and humidity before being dried.

In a fluid energy mill the material to be milled is entrained in an airstream and the particles caused to collide with one another by turbulence in the air stream. However, the energy input to the powder surface tends to produce a phase change to an amorphous state. One possible solution to this problem would be to mill at a reduced temperature. The material to be milled is likely to be more brittle and friable, resulting in a lower energy input to each powder particle. Also phase change reactions tend to proceed more slowly at lower temperatures. To be effective temperatures well below 0° C. are required. One problem with this approach is that the milling fluids most commonly used, nitrogen and air, become less effective as their temperature drops. In particular the exit velocity of the gas from the milling nozzles becomes too low.

We have now found that this problem can be overcome by using helium as milling fluid. The process provides finely milled, highly crystalline material containing substantially no amorphous material. A surprising advantage is that build up of scale in the mill during milling is much reduced. Less scale is deposited and the scale which is deposited is less hard and easier to remove.

Therefore, according to the present invention there is provided a method for producing fine, highly crystalline material consisting of fluid energy milling of crystalline material using a milling fluid comprising helium at reduced temperature.

Pure helium can be used or a mixture of helium and another gas. Thus, for example, nitrogen and/or air can be mixed with helium. Pure helium is preferred. Preferably the milling temperature falls within the range of −30 to −120° C., more preferably in the range −50 to −70° C.

The milling process may be applied to any crystalline material. However it may particularly be used to mill medicament powders, especially medicament powders intended for administration by inhalation. It is particularly advantageous when applied to soft powders which are difficult to mill to a fine uniform particle size.

The particle size of the product is controlled in the conventional manner by adjusting pressure and flow rate of the milling fluid and feed rate of the material to be milled. Any equipment conventionally used in combination with a fluid energy mill to help control product particle size distribution can also be used in conjunction with the claimed method. The reduced tendency to form scale is particularly advantageous when a classifier is used in conjunction with the mill.

We have also found that it is possible to produce extra fine powder by the method described above. Milled powders with a median particle size as low as 1 micron can be produced. The lower limit of powder median particle size which is produced by conventional fluid energy milling is around 2 to 3 micron.

The amount of amorphous material in a sample of milled powder can be assessed in a number of ways. Differential Scanning Calorimetry (DSC) will show the heat of crystallisation in a sample containing amorphous material. Alternatively the change in weight of a sample exposed to an atmosphere of controlled temperature and humidity can give a measure of the change in amorphous content. In both methods the apparatus is calibrated using samples of known crystalline content and the unknown sample measured by comparing the magnitude of the measurement for the unknown with the known samples.

Also, amorphous substances usually have a substantially higher specific surface area than the corresponding crystalline substance. Thus, when a powder with an appreciable amorphous content crystallises the specific surface area falls. When a powder produced by conventional milling with a substantial amorphous content is stored in contact with the atmosphere the amorphous material tends to crystallise over a period of time. Within a few days, or weeks at most, surface area falls to a substantially stable value.

Accordingly, in the context of the present invention a powder may be considered to have substantially no amorphous content if its specific surface area does not change substantially when stored in a container open to the atmosphere for a week or more. The change in surface area should preferably be no more than 20% of the initial value, more preferably no more than 10% and most preferably no more than 5%. Alternatively a powder would be considered to have substantially no amorphous content if the level immediately after milling as measured by weight change under controlled relative humidity or DSC is less than 5%, more preferably less than 2% and most preferably less than 1%.

Surface area can be measured by gas absorption using the Brunauer-Emmet-Teller method or by air permeametry using the Blaine method. Results given here relate to the latter method which is described in the standard method of the l'Association Francaise de Normalisation (AFNOR) no P 15-442 March 1987.

Weight change under controlled relative humidity is measured using a DVS 1 dynamic vapour sorption apparatus. A small weighed sample is placed in a microbalance pan and held at constant temperature of 25° C. and a relative humidity of 75%. Weight change is measured as a function of time over a period of at least 5 hours. The plot of weight v time shows a peak which is proportional to the proportion of amorphous material present. The equipment is calibrated with samples of known amorphous content produced by mixing fully crystalline and fully amorphous materials.

DSC measurements were carried out using a Seiko RDC 220 system. The sample is weighed into the measuring pan and held at a temperature below the recrystallisation temperature for 30 minutes under a flow of dry nitrogen to remove any surface moisture. The sample was then heated at a constant rate of 20° C. per minute. The exothermic peak due to recrystallisation is measured. As above the method is calibrated using samples of known amorphous content.

EXAMPLE

A two inch diameter pancake mill was used for the experiments. Helium is introduced to the circumference of the mill and powder to be milled is blown in through a venturi orifice also entering through the circumference of the milling chamber. Milled product, entrained in the milling fluid, exits through a central outlet. The temperature of the milling gas and/or the feed gas can be controlled.

The table below gives results obtained when milling triamcinolone acetonide (TAA) according to the present invention. The same feed was used in all cases and the starting material had a median particle size (d50) as measured by Malvern particle size analyser of around 25 micron. The gas used was helium or nitrogen in all cases.

Surface area was measured using the Blaine air permeability method. Where samples were stored for ageing trials the samples were kept in a 60% relative humidity atmosphere at 25° C.

Run 1 and Run 2 compare the effects of room temperature helium and nitrogen as milling gas. Helium gives a finer, higher surface area product but both products have a relatively high amorphous content.

Run 3 used nitrogen at −7° C. as milling gas. Again a relatively high amorphous content was produced.

Run 4 and Run 5 used cold helium as the milling and carrier gas. The product had no detectable amorphous content and was also significantly finer than would be expected given the milling conditions

|  | Run 1 | Run 2 | Run 3 | Run 4 | Run 5 |
|---|---|---|---|---|---|
| Feeding rate (kg/h) | 0.1 | 1 | 0.1 | 1 | 1 |
| Milling pressure (bar) | 4 | 5 | 7 | 5 | 5 |
| Feed gas pressure (bar) | 5 | 7 | 9 | 7 | 7 |
| Gas | Helium | Nitrogen | Nitrogen | Helium | Helium |
| Temperature (° C.) | Room T | Room T | −7 | −65 | −50 |
| mill size (inches) | 2 | 4 | 2 | 4 | 4 |
| Product Sw ($m^2/g$) | 3.2 | 1.5 | 1.2 | 3.0 | 3.3 |
| Product Sw ($m^2/g$) after one week | — | — | — | 2.9 | — |
| Product Sw ($m^2/g$) after two weeks | — | — | — | — | 3.3 |
| Product d50 (μm) | — | — | — | 1.5 | 1.5 |
| Amorphous content (%) | 7.6 | 3.2 | 5.8 | n.d. | n.d. | n.d. = not detected

Product from Run 5 was tested in an Ultrahale® device and the results compared with product milled in the conventional way. The Ultrahaler® is a dry powder inhaler whose basic operation is described in EP 407 028.

A compact was produced by compressing a mixture of 5% milled product with 95% lactose with a median particle size of 50 micrometer. The compact is loaded into the inhaler and doses cut off from it using a blade. Up to 200 doses can be obtained from each device. The important parameters are dose uniformity and the percentage respirable fraction of medicament produced in each dose.

For product produced by conventional means the mean respirable fraction produced was 44% and 83% of the doses cut were within 20% of their nominal weight. For product produced under the conditions of Run 5 the mean respirable fraction was 40% but the percentage of doses within 20% of nominal weight rose to 90%.

What is claimed is:

1. A method for producing a fine, highly crystalline material product, the method comprising fluid energy milling triamcinolone acctonide using a milling fluid comprising helium gas, wherein the product has an amorphous content of less than 5% and a median particle size of less than 10 microns, and the temperature of the milling fluid is between −30° C. and −120° C.

2. The method according to claim 1, wherein the milling fluid consists of helium gas.

3. The method according to claim 1, wherein the temperature of the milling fluid is between −50° C. and −70° C.

4. The method according to claim 1, wherein the product has an amorphous content of less than 2%.

5. The method according to claim 4, wherein the product has an amorphous content of less than 1%.

6. The method according to claim 1, wherein the product comprises a medicament powder in a form suitable for inhalation.

7. The crystalline material produced by a method according to claim 1.

8. The crystalline material according to claim 7 containing substantially no amorphous content and having a median particle size of less than 2 microns.

* * * * *